United States Patent
Ueno et al.

(10) Patent No.: US 6,900,333 B2
(45) Date of Patent: May 31, 2005

(54) PROCESS FOR THE PREPARATION OF 1, 2-DICHLORETHANE FREE CRYSTALS OF ZONISAMIDE

(75) Inventors: Yoshikazu Ueno, Osaka (JP); Yasujiro Kimura, Toyonaka (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 10/733,565

(22) Filed: Dec. 12, 2003

(65) Prior Publication Data

US 2004/0138473 A1 Jul. 15, 2004

Related U.S. Application Data

(60) Continuation of application No. 10/462,726, filed on Jun. 17, 2003, now abandoned, which is a division of application No. 10/340,601, filed on Jan. 13, 2003, now abandoned.

(51) Int. Cl.$^7$ .......................................... C07D 261/20
(52) U.S. Cl. ..................................................... 548/241
(58) Field of Search ........................................ 548/241

(56) References Cited

U.S. PATENT DOCUMENTS

| | | | |
|---|---|---|---|
| 4,172,896 A | 10/1979 | Uno et al. | |
| 4,533,764 A | 8/1985 | Chang et al. | |
| 5,030,643 A | 7/1991 | Bernstein et al. | |
| 5,082,669 A | 1/1992 | Shirai et al. | |
| 5,786,374 A | 7/1998 | Farooq et al. | |
| 5,811,547 A | 9/1998 | Nakamichi et al. | |
| 2003/0036556 A1 | 2/2003 | Jennings | |
| 2003/0054041 A1 | 3/2003 | Lemmens et al. | |

FOREIGN PATENT DOCUMENTS

| | | |
|---|---|---|
| FR | 2 428 033 | 1/1980 |
| JP | 53-77057 | 7/1978 |
| JP | 54-163570 | 12/1979 |
| JP | 54-163823 | 12/1979 |
| JP | 63-150220 | 6/1988 |
| WO | 03/020708 | 3/2003 |
| WO | 03/072552 | 9/2003 |

OTHER PUBLICATIONS

Lisgarten et al., "The structure of (1,2-Benzisoxazol-3-yl)methanesulfonamide: A Novel Antiepileptic Drug", Acta Cryst., C44, pp. 2013-2016, 1988.
I. Nagamoto et al., "A Solvent Used for Antiepileptic Drugs Increases Serum and Brain Zonisamide Concentrations Seizure-Susceptible EL Mice", Epilepsy & Behavior, 2, 357-362 (2001).
Hitoshi Uno et al., "Studies on 3-Substituted 1,2-Benzisoxazole Derivatives. V$^{1)}$ Electrophilic Substitutions of 1,2-Benzisoxazole-3-acetic Acid", Chem. Pharm. Bull., vol. 26, No. 11, pp. 3498-3503, 1978.
Hitoshi Uno et al., "Studies on 3-Substituted 1,2-Benzisoxazole Derivatives. 6. Synthesis of 3-(Sulfamoylmethyl)-1,2-benzisoxazole Derivatives and Their Anticonvulsant Activities", Journal of Medicinal Chemistry, vol. 22, No. 2, pp. 180-183, 1979.
Masanao Shimizu et al., "Research and Development of Zonisamide, a New Type of Antiepileptic Drug", Yakugaku Zasshi, vol. 116, No. 7, pp. 533-547, 1996.
"Impurities: Guideline for Residual Solvents", ICH Harmonised Tripartite Guideline, International Conference on Harmonisation of Technical Requirements for Registration of Pharmaceuticals for Human Use, pp. 1-16, Jul. 17, 1997.

*Primary Examiner*—Patricia L. Morris
(74) *Attorney, Agent, or Firm*—Wenderoth, Lind & Ponack, L.L.P.

(57) ABSTRACT

A process for the preparation of crystals of zonisamide containing residual 1,2-dichloroethane of not more than 5 ppm, by adding an aqueous $C_{2-4}$ alcohol to crystals of zonisamide containing residual 1,2-dichloroethane of more than 5 ppm, removing the 1,2-dichloroethane by azeotropic distillation, followed by collecting the precipitated crystals from the residual mixture.

7 Claims, No Drawings

PROCESS FOR THE PREPARATION OF 1, 2-DICHLORETHANE FREE CRYSTALS OF ZONISAMIDE

This application is a Continuation application of application Ser. No. 10/462,726, filed Jun. 17, 2003, now abandoned, which is a Divisional application of application Ser. No. 10/340,601, filed Jan. 13, 2003, now abandoned.

TECHNICAL FIELD

The present invention relates to a process for the preparation of crystals of zonisamide (chemical name: 1,2-benzisoxazole-3-methanesulfonamide), which is useful as an antiepileptic agent. More particularly, the present invention relates to a process for efficiently preparing crystals of zonisamide containing residual 1,2-dichloroethane of not more than 5 ppm.

BACKGROUND ART

Zonisamide has widely been used as an antiepileptic agent in Japan and the United States. Zonisamide and processes for the preparation thereof are disclosed in JP-A-53-77057, U.S. Pat. No. 4,172,896 and JP-A-54-163823. In addition, Yakugaku-Zasshi, vol. 116, p. 533–547 (1996) discloses that zonisamide has actually been prepared using as an intermediate 1,2-benzisoxazole-3-methanesulfonyl chloride, which is obtained by sulfonation and decarboxylation of 1,2-benzisoxazol-3-acetic acid. Further, the solvent for the above sulfonation and decarboxylation is dichloromethane in the process disclosed in Yakugaku-Zasshi, vol. 116, p. 533–547 (1996), and 1,2-dichloroethane in the process disclosed in JP-A-53-77057.

The solvent used in the preparation of a drug substance cannot completely be removed by practical manufacturing techniques, which are in actuality employed in the production. Therefore, in the preparation of drug substance wherein plural steps are serially carried out till the final step, each solvent used in each step may possibly remain in a residual amount in the drug substance. Further, residual solvents in the drug substance usually cannot be useful for the therapeutic benefits of the drug substance, and contrarily, there may be caused a problem of safety of a patient according to the kinds of residual solvents and a concentration thereof. In terms of improving and increasing the safety of drugs, "IMPURITIES: GUIDELINE FOR RESIDUAL SOLVENTS", ICH Harmonized Tripartite Guideline, 17 Jul. 1997 was made in INTERNATIONAL CONFERENCE ON HARMONISATION OF TECHNICAL REQUIREMENTS FOR REGISTRATION OF PHARMACEUTICALS FOR HUMAN USE (ICH).

Since a solvent may play an important role in increasing the yield rate or in determination of physical properties of drug substance such as crystal form, purity, solubility, etc., even if such a solvent is known to be toxic, there may be many cases that the use thereof in the preparation of drug substance cannot be avoided in terms of risk-benefits. In such cases, this guideline decrees that a concentration of a residual solvent in the drug substance should be not more than a limit which is toxicologically acceptable.

A solvent for the preparation of the intermediate for zonisamide, 1,2-benzisoxazole-3-methanesulfonyl chloride, is 1,2-dichloroethane rather the dichloromethane. This is because, during the decarboxylation, which is carried out after the sulfonation of 1,2-benzisoxazole-3-acetic acid, the reaction mixture requires to be heated at about 60° C., which is higher than the boiling point of dichloromethane. In addition, 1,2-dichloroethane can be used as well in the step of preparation of zonisamide by reacting 1,2-benzisoxazole-3-methanesulfonyl chloride with ammonia. However, when zonisamide is prepared using 1,2-dichloroethane, the residual concentration thereof should be not more than 5 ppm as defined in the above-mentioned guideline "IMPURITIES: GUIDELINE FOR RESIDUAL SOLVENTS". This guideline is not applied to the drugs, which are already on market, but it is very important to prepare a drug substance complying with this guideline in terms of safety of drugs.

The removal of residual solvent is usually carried out by drying. However, it is very difficult to completely remove an occluded solvent by a drying method being actually employed in the production. U.S. Pat. No. 4,533,746 discloses a method of removing the solvent by distillation in purification of bisphenols, wherein the solvent occluded in bisphenols is released and removed from bisphenol melted in water. This method utilizes the characteristic of bisphenol, which melts in water by heating, and thereby the occluded solvent is released. On the other hand, zonisamide cannot melt even by heating in water, and hence, this method cannot be applied for removal of the solvent occluded in crystals of zonisamide.

SUMMARY OF INVENTION

The present inventors have intensively studied a process for the preparation of crystals of zonisamide having a high safety and complying with the above-mentioned guideline, and have found that the desired crystals of zonisamide containing residual 1,2-dichloroethane of not more than 5 ppm can easily be obtained even from crystals of zonisamide containing 1,2-dichloroethane in a high concentration, by using an aqueous $C_{2-4}$ alcohol, i.e., by the steps of adding an aqueous $C_{2-4}$ alcohol to said crystals and distilling the resulting mixture, followed by crystallization, without equipping any additional apparatus to existing ones, or without repetition of recrystallization, and further there are no affects on the yield thereof, and finally the present inventors have accomplished the present invention.

DETAILED DESCRIPTION OF INVENTION

The present invention provides a process for the preparation of crystals of zonisamide containing residual 1,2-dichloroethane of not more than 5 ppm, which comprises adding an aqueous $C_{2-4}$ alcohol to crystals of zonisamide containing residual 1,2-dichloroethane of more than 5 ppm, usually more than 5 ppm to 200000 ppm, removing said 1,2-dichloroethane by azeotropic distillation, followed by collecting the crystals from the residual mixture.

More particularly, the present invention provides a process for the preparation of crystals of zonisamide containing residual 1,2-dichloroethane of not more than 5 ppm, which comprises the following steps (a), (b), (c) and (d):

(a) dissolving crystals of zonisamide containing residual 1,2-dichloroethane of more than 5 ppm in an aqueous $C_{2-4}$ alcohol, and subjecting the mixture to azeotropic distillation;

(b) stopping the distillation after the azeotropic distillation of said 1,2-dichloroethane is completed;

(c) cooling the residual mixture obtained in the above step (b); and (d) collecting crystals of zonisamide precipitated in the above step (c) by filtration and drying thereof.

The present invention also provides a process for the preparation of crystals of zonisamide containing residual 1,2-dichloroethane of not more than 5 ppm, which comprises the above steps (a) and (b), and the following steps (c1) and (d1):

(c1) adding the same $C_{2-4}$ alcohol as used in the step (a) and/or water to the residual mixture obtained in the above step (b), and dissolving the mixture with heating, and cooling thereof; and (d1) collecting crystals of zonisamide precipitated in the above step (c1) by filtration and drying thereof.

The "aqueous $C_{2-4}$ alcohol" means a mixture of water and a $C_{2-4}$ alcohol, and the "$C_{2-4}$ alcohol" includes, for example, ethanol, propanol, isopropanol, and 2-butanol. The "aqueous $C_{2-4}$ alcohol" is preferably aqueous ethanol, aqueous propanol, or aqueous isopropanol, among them aqueous isopropanol is most preferable.

The "crystals of zonisamide containing residual 1,2-dichloroethane of more than 5 ppm" (hereinafter, occasionally referred to as "starting crystals of zonisamide") mean crystals of zonisamide containing residual 1,2-dichloroethane in the range of more than 5 ppm to 200000 ppm, although the higher limit of the concentration of said 1,2-dichloroethane is not necessarily specified. In general, "crystals of zonisamide containing residual 1,2-dichloroethane of more than 5 ppm" are crystals of zonisamide containing residual 1,2-dichloroethane in the range of 8 ppm to 150000 ppm.

The step of removing 1,2-dichloroethane by azeotropic distillation is usually carried out subsequently to the step of dissolving the starting crystals of zonisamide in an aqueous $C_{2-4}$ alcohol. The temperature for dissolving the starting crystals of zonisamide is not necessarily specified, but it is usually in the range of from 30° C. to a boiling point of the $C_{2-4}$ alcohol to be used.

The starting crystals of zonisamide are mixed with an aqueous $C_{2-4}$ alcohol in an amount of 5 to 15 parts by volume per 1 part by weight of the starting crystals of zonisamide. In other words, 1 g of dry weight of zonisamide is mixed with 5 to 15 ml of an aqueous $C_{2-4}$ alcohol. The starting crystals of zonisamide are preferably mixed with an aqueous $C_{2-4}$ alcohol in an amount of 5.2 to 10.4 parts by volume per 1 part by weight of the starting crystals of zonisamide. Preferable aqueous $C_{2-4}$ alcohol is usually a $C_{2-4}$ alcohol containing water in 35 to 65% by volume, and more preferable one is a $C_{2-4}$ alcohol containing water in 40 to 60% by volume, and further preferable one is a $C_{2-4}$ alcohol containing water in 45 to 55% by volume. In the present specification, for example, the 55% by volume aqueous $C_{2-4}$ alcohol means a mixture of water in 55 parts by volume and a $C_{2-4}$ alcohol in 45 parts by volume.

The distillation may be carried out either under atmospheric pressure or under reduced pressure, but preferably is carried out under atmospheric pressure. The temperature at which the distillation is started is usually an azeotropic point of 1,2-dichloroethane-an $C_{2-4}$ alcohol-water. For example, the azeotropic point of 1,2-dichloroethane-ethanol-water is 66.7° C., and the azeotropic point of 1,2-dichloroethane-isopropanol-water is 69.7° C., but these azeotropic points may vary under the influences of barometric pressure when the distillation is carried out or of molar elevation of boiling point, etc. The temperature at which the distillation is stopped may vary according to the kinds of the aqueous $C_{2-4}$ alcohol to be used, and it is usually in the range of from 78° C. to 100° C., preferably in the range of from 85° C. to 100° C., and more preferably in the range of 90° C. to 100° C.

After the distillation is stopped, the residual mixture is cooled in situ to precipitate crystals of zonisamide containing residual 1,2-dichloroethane of not more than 5 ppm. In addition, crystals of zonisamide may be precipitated in the middle of the distillation procedure. Therefore, in cases that crystals are precipitated in the residual mixture after the distillation is stopped, the same $C_{2-4}$ alcohol as that to be used in the distillation procedure and/or water are added to the residual mixture after the distillation is stopped, and the resulting mixture is heated again to dissolve the crystals, and then cooled to precipitate crystals of zonisamide containing residual 1,2-dichloroethane of not more than 5 ppm. For instance, when an aqueous isopropanol is used in the distillation procedure, water and/or isopropanol are added to the residual mixture after the distillation in such an amount that the ratio of water and isopropanol in the residual mixture after the distillation becomes in the range of 35:65 to 65:35, preferably in the range of 40:60 to 60:40, more preferably in the range of 45:55 to 55:45, and the total volume of water and isopropanol becomes 2 to 20 parts by volume, preferably 8 to 14 parts by volume, per 1 part by weight of the starting crystals (in dry state) of zonisamide, and the resulting mixture is heated again and then cooled. This step is preferably carried out together with the purification using activated carbon.

The crystallized zonisamide is collected by filtration and dried by a conventional method to give crystals of zonisamide containing residual 1,2-dichloroethane of not more than 5 ppm, and in many cases, there are obtained crystals of zonisamide containing residual 1,2-dichloroethane of less than detection limit. The crystals of zonisamide to be collected by filtration are dried at a temperature of from 60 to 100° C., preferably at a temperature of from 70 to 90° C., for 8 to 24 hours, preferably for 12 to 18 hours. Vacuum drying is more preferable.

The starting crystals of zonisamide to be used in the present process may be prepared according to the method disclosed in Reference Example 3 and Example 1 of JP-A-53-77057, except for the solvent in Example 1. That is, it is prepared by reacting 1,2-benzisoxazole-3-methanesulfonyl chloride with ammonia in 1,2-dichloroethane as a solvent, concentrating the reaction mixture, adding water to the resulting residue, followed by collecting the precipitated crystals to give wet crystals containing zonisamide in an amount of about 85% by weight.

The wet crystals containing zonisamide in an amount of about 85% by weight obtained in the above process are recrystallized from 50% aqueous isopropanol in usual manner, and the resulting crystals are dried under reduced pressure at a temperature of from 40 to 80° C. for 18 hours to give crystals of zonisamide containing residual 1,2-dichloroethane in a concentration of from 8 to 14 ppm.

BEST MODE FOR CARRYING OUT THE INVENTION

The present invention is illustrated in more detail by the following Examples, but the present invention should not be construed to be limited thereto. The content of 1,2-dichloroethane in crystals of zonisamide was measured by gas chromatography.

EXAMPLE 1

To wet crystals (60 g) containing zonisamide in an amount of about 85% by weight prepared by using 1,2-dichloroethane in the method disclosed in Reference Example 3 and Example 1 of JP-A-53-77057 was added 50 vol % aqueous isopropanol (500 ml), and 320 ml of the solvent was removed by evaporation at a temperature of from 76 to 100° C. under stirring. To the residual mixture were added water (10 ml), isopropanol (200 ml) and activated carbon (8 g), and the mixture was dissolved with heating. The activated carbon was separated by filtration, and washed with 50% aqueous isopropanol (80 ml). The filtrate and the washing were combined and cooled. The precipitated crystals were collected by filtration, washed with water (100 ml), and dried at 80° C. for 16 hours to give crystals of zonisamide (48.5 g). The content of 1,2-dichloroethane in the crystals was less than 1 ppm (less than detection limit).

EXAMPLES 2–3

The same procedures as Example 1 were repeated except that the water content in the aqueous isopropanol and the amount of the aqueous isopropanol were changed. The results are shown in Table 1.

TABLE 1

| Item | Example 2 | Example 3 |
| --- | --- | --- |
| Water content in aqueous isopropanol (vol %) | 65 | 50 |
| Amount of aqueous isopropanol, (ml) | 450 | 310 |
| Evaporation temperature (° C.) | 76–100 | 80–100 |
| Amount of evaporated solvent (ml) | 250 | 205 |
| Yield of crystals (g) | 49.0 | 47.8 |
| Content of residual 1,2-dichloroethane (ppm) | <1 (less than DL) | <1 (less than DL) |

(DL: detection limit)

EXAMPLE 4

To the same wet crystals (60 g) containing zonisamide in an amount of about 85% by weight as used in Example 1 were added 50 vol % aqueous isopropanol (300 ml), water (7.5 ml) and 1,2-dichloroethane (8.8 g), and 210 ml of the solvent was removed by evaporation at a temperature of from 79 to 100° C. under stirring. The residual mixture was cooled, and the precipitated crystals were collected by filtration to give wet crystals of zonisamide (56.7 g). The content of 1,2-dichloroethane in the wet crystals of zonisamide was less than 1 ppm (less than detection limit). The wet crystals were dried at 80° C. for 16 hours to give dried crystals of zonisamide (49.9 g).

EXAMPLE 5

To the dried crystals of zonisamide (50.0 g) was added 55 vol % aqueous isopropanol (260 ml), and thereto were further added 1,2-dichloroethane (7.5 g) and water (7.5 g), and the mixture was stirred at a stirring velocity of 220 rpm. Then, the mixture was heated until the inner temperature thereof became 100° C., and 160 ml of the solvent was removed by evaporation. The residual mixture was cooled, and thereto were added water (145 ml), isopropanol (230 ml) and activated carbon (9.1 g), and the mixture was heated at a temperature of from 80 to 83° C. for one hour. The activated carbon was separated by filtration, and washed with 50% aqueous isopropanol (175 ml). The filtrate and the washing were combined and cooled. After cooled to about 8° C., the precipitated crystals were collected by filtration and washed with water (136 ml). The crystals were dried with air blowing at 100° C. for 16 hours to give the dried crystals of zonisamide (47.1 g).

INDUSTRIAL APPLICABILITY

By conventional methods for recrystallization, crystals of zonisamide containing residual 1,2-dichloroethane of not more than 5 ppm could not be obtained from the starting crystals of zonisamide prepared using 1,2-dichloroethane. On the contrary, the content of the residual 1,2-dichloroethane in the crystals of zonisamide prepared by the Examples of the present process is less than 1 ppm (less than detection limit), which is far lower than required 5 ppm. As shown in Example 4, the present process is effective and applicable even if there is a large residual amount of 1,2-dichloroethane in the starting crystals of zonisamide. In addition, as shown in Example 5, the yield of crystals of zonisamide is not so reduced even by subjecting them to the present process.

As explained in the above, according to the method of the present invention, crystals of zonisamide containing residual 1,2-dichloroethane of not more than 5 ppm can effectively be obtained from the starting crystals of zonisamide prepared using 1,2-dichloroethane as the solvent.

What is claimed is:

1. A process for the preparation of crystals of 1,2-benzisoxazole-3-methanesulfonamide containing residual 1,2-dichloroethane of not more than 5 ppm, which comprises adding an aqueous $C_{2-4}$ alcohol to crystals of 1,2-benzisoxazole-3-methanesulfonamide containing residual 1,2-dichloroethane of more than 5 ppm, removing said 1,2-dichloroethane by azeotropic distillation to obtain a residual mixture, followed by collecting precipitated crystals of 1,2-benzisoxazole-3-methanesulfonamide containing not more than 5 ppm of 1,2-dichloroethane from the residual mixture.

2. A process for the preparation of crystals of 1,2-benzisoxazole-3-methanesulfonamide containing residual 1,2-dichloroethane of not more than 5 ppm, which comprises:
   (a) dissolving crystals of 1,2-benzisoxazole-3-methanesulfonamide containing residual 1,2-dichloroethane of more than 5 ppm in an aqueous $C_{2-4}$ alcohol, and subjecting the resultant mixture to azeotropic distillation;
   (b) stopping the distillation after the azeotropic distillation of said 1,2-dichloroethane is completed to obtain a residual mixture;
   (c) cooling the residual mixture to precipitate crystals of 1,2-benzisoxazole-3-methanesulfonamide containing not more than 5 ppm of 1,2-dichloroethane; and
   (d) collecting the precipitated crystals of 1,2-benzisoxazole-3-methanesulfonamide by filtration and drying thereof.

3. A process for the preparation of crystals of 1,2-benzisoxazole-3-methanesulfonamide containing residual 1,2-dichloroethane of not more than 5 ppm, which comprises:
   (a) dissolving crystals of 1,2-benzisoxazole-3-methanesulfonamide containing residual 1,2-dichloroethane of more than 5 ppm in an aqueous $C_{2-4}$ alcohol, and subjecting the resultant mixture to azeotropic distillation;
   (b) stopping the distillation after the azeotropic distillation of said 1,2-dichloroethane is completed to obtain a residual mixture;
   (c1) adding the same $C_{2-4}$ alcohol as used in (a) and/or water to the residual mixture obtained in (b), dissolving the residual mixture with heating, and cooling thereof to precipitate crystals of 1,2-benzisoxazole-3-methanesulfonamide containing not more than 5 ppm of 1,2-dichloroethane; and
   (d1) collecting the precipitated crystals of 1,2-benzisoxazole-3-methanesulfonamide by filtration and drying thereof.

4. The process according to claim 1, wherein the aqueous $C_{2-4}$ alcohol is an aqueous isopropanol.

5. The process according to claim 1, wherein the aqueous $C_{2-4}$ alcohol is isopropanol containing water in an amount of 35 to 65% by volume.

6. The process according to claim 2, wherein the temperature at which the distillation is stopped is in the range of from 78° C. to 100° C.

7. A process for the preparation of crystals of 1,2-benzisoxazole-3-methanesulfonamide containing residual 1,2-dichloroethane of not more than 5 ppm, which comprises adding an aqueous $C_{2-4}$ alcohol to crystals of 1,2-benzisoxazole-3-methanesulfonamide containing residual 1,2-dichloroethane of more than 5 ppm and distilling the resulting mixture, to remove at least some of the residual 1,2-dichloroethane from the crystals of 1,2-benzisoxazole-3-methanesulfonamide containing residual 1,2-dichloroethane of more than 5 ppm.

* * * * *